(12) United States Patent
Heinelt et al.

(10) Patent No.: US 6,737,423 B2
(45) Date of Patent: May 18, 2004

(54) SUBSTITUTED HETEROCYCLO-NORBORNYLAMINO DERIVATIVES, PROCESSES FOR THEIR PREPARATION, THEIR USE AS MEDICAMENTS OR DIAGNOSTICS, AND MEDICAMENTS COMPRISING THEM

(75) Inventors: Uwe Heinelt, Wiesbaden (DE); Hans-Jochen Lang, Hofheim (DE); Klaus Wirth, Kriftel (DE); Hans-Willi Jansen, Niedernhausen (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 32 days.

(21) Appl. No.: 10/020,241

(22) Filed: Dec. 18, 2001

(65) Prior Publication Data

US 2002/0173500 A1 Nov. 21, 2002

(30) Foreign Application Priority Data

Dec. 19, 2000 (DE) .......................... 100 63 294

(51) Int. Cl.$^7$ .................... C07D 213/38; C07D 307/52; A61K 31/44
(52) U.S. Cl. .................... 514/247; 514/252.1; 514/256; 514/357; 514/365; 514/400; 514/427; 514/438; 514/471; 544/224; 544/294; 544/336; 546/285; 548/202; 548/335.5; 548/528
(58) Field of Search ................ 544/224, 294, 544/336; 546/285; 548/202, 528, 335.5; 514/247, 256, 252.1, 357, 365, 400, 427, 438, 471

(56) References Cited

U.S. PATENT DOCUMENTS

| | | | |
|---|---|---|---|
| 4,024,274 A | 5/1977 | Druckrey et al. | 424/282 |
| 6,005,010 A | 12/1999 | Schwark et al. | 514/616 |
| 6,355,660 B1 * | 3/2002 | Ricks et al. | 514/357 |
| 2001/0023257 A1 | 9/2001 | Heinelt et al. | 514/524 |

FOREIGN PATENT DOCUMENTS

| | | |
|---|---|---|
| DE | 199 60 204 A1 | 6/2001 |
| EP | 0 825 178 B1 | 2/1998 |
| WO | WO 96 40141 | 12/1996 |
| WO | WO 01 44164 A1 | 6/2001 |

OTHER PUBLICATIONS

Simone, Oncology: Introduction, Cecil Textbook of Medicine, 20th Edition, vol. 1, pp. 1004–1010, 1996.*

Cavet et al., Half–lives of plasma membrane Na + /H + exchangers NHE1–3: plasma membrane NHE2 has a rapid rate of degradation, Am. J. Physiol. Cell Physiol. 281: C2039–2048, 2001.*

Gekle et al., Inhibition of Na + —H + exchange impairs receptor–mediated albumin endocytosis in renal proximal tubule–derived epithelial cells from opossum, Journal of Physiology, 520(3), pp. 709–721, 1999.*

Jan–Robert Schwark, et al., S3226, a novel inhibitor of Na+/H$^+$ exchanger subtype 3 in various cell types, Pflügers Arch—Eur J Physiol 436:797–800 (1998).

Abstract for EP 0 825 178 B1, esp@cenet database, 1998.

Abstract for DE 199 60 204 A1, esp@cenet database, 2001.

* cited by examiner

*Primary Examiner*—Deepak Rao
(74) *Attorney, Agent, or Firm*—Finnegan, Henderson, Farabow, Garrett & Dunner, L.L.P.

(57) ABSTRACT

Substituted heterocyclo-norbornylaminoderivatives having:
a) an exo-configuration nitrogen and an endo-fused five-membered ring or six-membered ring of the formula (I) or
b) an exo-configuration nitrogen and an exo-fused five-membered ring or six-membered ring of the formula (I a),

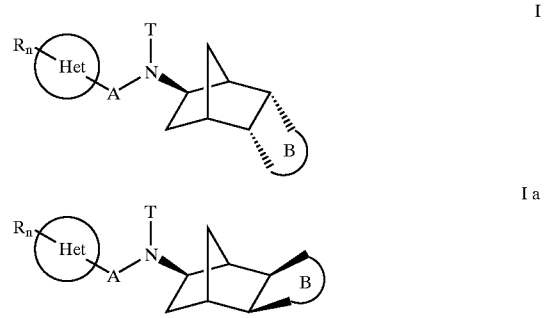

wherein $R_n$, Het, A, B and T have the meanings given in the claims. These compounds have a variety of uses. They can be used as antihypertensives, for the reduction or prevention of is chemically induced damage, as pharmaceuticals for surgical interventions, for the treatment of ischemia of the nervous system, including stroke and cerebral edema, for the treatment of ischemia due to shock and disturbed respiratory drive, for the treatment of snoring, as a laxative, as an agent against ectoparasites, for the prevention of gallstone formation, as an antiatherosclerotic, as an agent against diabetic late complications, cancers, fibrotic disorders, endothelial dysfunction, organ hypertrophy, and organ hyperplasia.

The compounds of the invention are inhibitors of the cellular sodium-proton antiporter. Additonally, the compounds of the invention influence the serum lipoproteins and can therefore be used for the prophylaxis and the regression of atherosclerotic changes.

34 Claims, No Drawings

SUBSTITUTED HETEROCYCLO-NORBORNYLAMINO DERIVATIVES, PROCESSES FOR THEIR PREPARATION, THEIR USE AS MEDICAMENTS OR DIAGNOSTICS, AND MEDICAMENTS COMPRISING THEM

This application claims the benefit of the filing date of German Patent Application Number 10063294.7-44, filed on Dec. 19, 2000, which application is hereby incorporated by reference.

One embodiment of the invention relates to substituted heterocyclo-norbornylamino derivatives having: a) an exo-configuration nitrogen and an endo-fused five-membered or six-membered ring of the formula (I), or b) an exo-configuration nitrogen and an exo-fused five-membered or six-membered ring of the formula (I a),

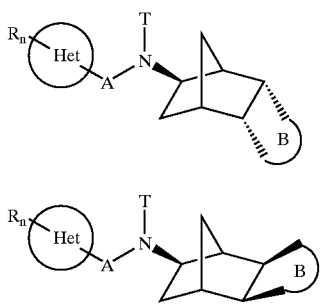

wherein:

A is $(C_1-C_4)$-alkylene;

T is $(C_1-C_4)$-alkyl or H;

B is a saturated or unsaturated carbon five-membered or six-membered ring, which is unsubstituted or is substituted, having 1–3 substituents chosen from oxo, hydroxyl, $(C_1-C_4)$-alkoxy, and $(C_1-C_4)$-alkyl;

Het is a 5- or 6-membered, saturated or unsaturated, heterocycle that contains up to four identical or different heteroatoms chosen from O, S, N, and Se;

R is OH, F, Cl, Br, I, CN, $NO_2$, phenyl, $CO_2R1$, $(C_1-C_4)$-alkyl, $(C_1-C_4)$-alkoxy, amino, $(C_1-C_4)$-alkylamino, di$(C_1-C_4)$-alkylamino, or amino-$(C_1-C_4)$-alkyl, wherein the alkyl radicals are unsubstituted or are completely or partly substituted by fluorine;

$R_1$ is H or $(C_1-C_4)$-alkyl, which is unsubstituted or completely or partly substituted by fluorine;

n0, 1, 2, 3 or 4, wherein, if n=2, 3 or 4, the substituents R are chosen independently of one another;

and their pharmaceutically tolerable salts or trifluoracetates.

Examples of compounds of the invention include those compounds having an exo-configuration nitrogen and endo-fused carbon five-membered or six-membered ring of the formula (I) and those compounds having an exo-configuration nitrogen and exo-fused carbon five-membered or six-membered ring of the formula (I a), wherein:

A is $(C_1-C_2)$-alkylene;

T is H or methyl;

B is a saturated or unsaturated carbon five-membered or six-membered ring;

Het is a 5- or 6-membered, saturated or unsaturated, heterocycle that contains up to three identical or different heteroatoms chosen from O, S, and N;

R is F, Cl, Br, iodine, amino, hydroxymethyl, OH, phenyl, $CO_2R1$, $(C_1-C_4)$-alkyl, or $(C_1-C_4)$-alkoxy, wherein the alkyl radicals are unsubstituted or completely or partly substituted by fluorine;

$R_1$ is H or $(C_1-C_4)$-alkyl, wherein the alkyl radical is unsubstituted or completely or partly substituted by fluorine;

n0, 1, 2 or 3, wherein, if n=2 or 3, the corresponding substituents R are chosen independently of one another;

and their pharmaceutically tolerable salts or trifluoracetates.

Further examples of compounds of the invention include those compounds having an exo-configuration nitrogen and endo-fused carbon five-membered or six-membered ring of the formula (I) and those compounds having an exo-configuration nitrogen and exo-fused carbon five-membered or six-membered ring of the formula (I a), wherein:

A is $(C_1-C_2)$-alkylene;

T is hydrogen;

B is a saturated or unsaturated carbon five-membered or six-membered ring;

Het is a 5- or 6-membered, saturated or unsaturated, heterocycle that contains up to two identical or different heteroatoms chosen from O, S, and N R is F, Cl, Br, $(C_1-C_4)$-alkoxy or $(C_1-C_4)$-alkyl, wherein the alkyl radicals are unsubstituted or completely or partly substituted by fluorine;

nis 0, 1 or 2, wherein, if n=2, the corresponding substituents R are chosen independently of one another;

and their pharmaceutically tolerable salts or trifluoracetates.

Even more examples of the compounds of the invention include those compounds having an exo-configuration nitrogen and endo-fused carbon five-membered or six-membered ring of the formula (I) and those compounds having an exo-configuration nitrogen and exo-fused carbon five-membered ring of the formula (I a) such as, for example:

exo/exo-(octahydro-4,7-methanoinden-5-yl)pyridin-3-ylmethylamine, (rac)-exo/endo-(octahydro-4,7-methanoinden-5-yl)pyridin-3-ylmethylamine, (+)-exo/endo-(octahydro-4,7-methanoinden-5-yl)pyridin-3-ylmethylamine, (−)-exo/endo-(octahydro-4,7-methanoinden-5-yl)pyridin-3-ylmethylamine, (rac)-exo/endo-(octahydro-4,7-methanoinden-5-yl)pyrazin-2-ylmethylamine, (+)-exo/endo-(octahydro-4,7-methanoinden-5-yl)pyrazin-2-ylmethylamine, (−)-exo/endo-(octahydro-4,7-methanoinden-5-yl)pyrazin-2-ylmethylamine, exo/endo-(decahydro-1,4-methanonaphthalen-2-yl)pyrazin-2-ylmethyl-amine, exo/endo-(octahydro-4,7-methanoinden-5-yl)thiophen-2-ylmethylamine, exo/endo-(octahydro-4,7-methanoinden-5-yl)thiophen-3-ylmethylamine, exo/endo-(3a,4,5,6,7,7a-hexahydro-3H-4,7-methanoinden-5-yl)pyridin-3-ylmethylamine, exo/endo-(3a,4,5,6,7,7a-hexahydro-1H-4,7-methanoinden-5-yl)pyridin-3-ylmethylamine, exo/endo-furan-3-ylmethyl-(octahydro-4,7-methanoinden-5-yl)amine, exo/endo-furan-2-ylmethyl-(octahydro-4,7-methanoinden-5-yl)amine,
exo/endo-(decahydro-1,4-methanonaphthalen-2-yl)pyridin-3-ylmethylamine,
exo/endo-(octahydro-4,7-methanoinden-5-yl)-(1 H-pyrrol-2-ylmethyl)amine,
exo/endo-(octahydro-4,7-methanoinden-5-yl)-pyrimidin-5-ylmethylamine
and their pharmaceutically tolerable salts or trifluoracetates.

More examples of compounds of the invention include those compounds having an exo-configuration nitrogen and endo-fused carbon five-membered or six-membered ring of the formula (I) and those compounds having an exo-configuration nitrogen and exo-fused carbon five-membered ring of the formula (I a) such as, for example:

exo/exo-(octahydro-4,7-methanoinden-5-yl)pyridin-3-ylmethylamine,
(rac)-exo/endo-(octahydro-4,7-methanoinden-5-yl)pyridin-3-ylmethylamine,
(+)-exo/endo-(octahydro-4,7-methanoinden-5-yl)pyridin-3-ylmethylamine,
(−)-exo/endo-(octahydro-4,7-methanoinden-5-yl)pyridin-3-ylmethylamine,
(rac)-exo/endo-(octahydro-4,7-methanoinden-5-yl)pyrazin-2-ylmethylamine,
(+)-exo/endo-(octahydro-4,7-methanoinden-5-yl)pyrazin-2-ylmethylamine,
exo/endo-(octahydro-4,7-methanoinden-5-yl)thiophen-2-ylmethylamine,
exo/endo-(3a,4,5,6,7,7a-hexahydro-3H-4,7-methanoinden-5-y l)pyrimidin-3-ylmethylamine,
exo/endo-(3a,4,5,6,7,7a-hexahydro-1H-4,7-methanoinden-5-yl)pyridin-3-ylmethylamine,
exo/endo-(decahydro-1,4-methanonaphthalen-2-yl)pyridin-3-ylmethylamine,
exo/endo-(octahydro-4,7-methanoinden-5-yl)-(1H-pyrrol-2-ylmethyl)amine,
exo/endo-(octahydro-4,7-methanoinden-5-yl)-pyrimidin-5-ylmethylamine
and their pharmaceutically tolerable salts or trifluoracetates.

Suitable acid addition salts of the compounds of the invention include salts of pharmacologically tolerable acids, for example halides (such as hydrochlorides), lactates, sulfates, citrates, tartrates, acetates, phosphates, methylsulfonates, p-toluenesulfonates, adipates, fumarates, gluconates, glutamates, glycerophosphates, maleates, and pamoates. This group also exemplifies some of the physiologically acceptable anions, in addition to trifluoracetates.

If a compound of the formula (I) or (I a) contains one or more asymmetric centers, these centers can have either the S or the R configuration. The compounds can be present as optical isomers, diastereomers, racemates, or mixtures thereof. However, the amino substituent on the norbornyl system must be exo and the ring endo- or exo-fused The alkyl or alkylene radicals mentioned can be either straight-chain or branched.

Suitable heterocycles include, inter alia:

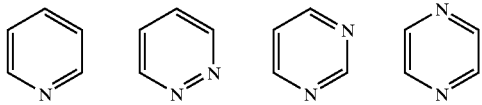

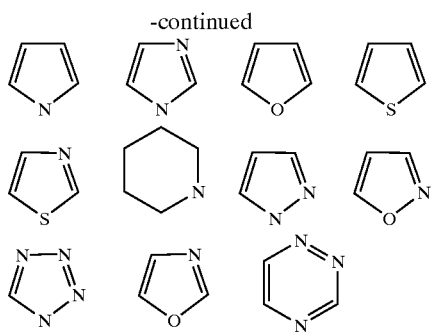

Another embodiment of the invention relates to a process for the preparation of the compounds of the formula (I) or (I a), which comprises a) reacting a compound of the formula (II) or (II a)

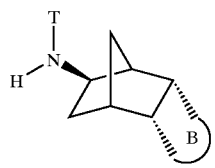

II

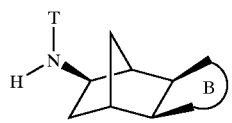

II a with a compound of the formula (III)

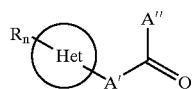

III in the presence of suitable reductants and possibly also Lewis acids directly to give compounds of the formula (I) or (I a), wherein T, B, Het and $R_n$ have the meanings indicated above; independently of one another A' corresponds to a bond or $(C_1-C_3)$-alkyl and A" corresponds to H or $(C_1-C_3)$-alkyl; and A' and A", together with the carbon atom of the carbonyl group, represent as many carbon atoms as A represents in formula (I) or (I a);

or b) isolating an intermediate of the formula (IV) or (IV a), formed from reacting compounds of the formulae (II), or (II a), with a compound of formula (III), and then converting the intermediate of the formula (IV) or (IV a) into the compounds of the formula (I) or (I a) by using suitable reductants,

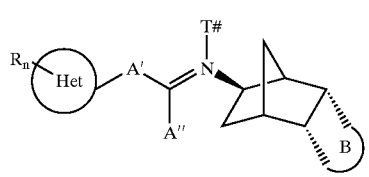

IV

-continued

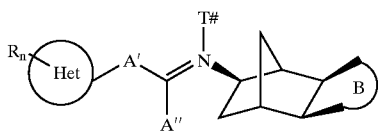

IVa wherein T# is a free electron pair or $(C_1-C_4)$-alkyl. When T# is $(C_1-C_4)$-alkyl, an iminium ion is formed, to which a counterion is assigned, such as, for example, chloride or tosylate, or c) reacting a compound of the formula (II) or (II a) with an alkylating agent of the formula (V),

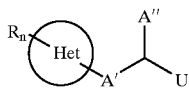

V wherein U is a nucleophilically substitutable group, such as for example a halogen, alkylsulfonates, or arylsulfonates, including Cl, Br, I, mesylate, or tosylate, and the other radicals are defined as described above. Here, the carbon atom to which U is bonded corresponds to the carbon atom of the carbonyl group of the compound of formula (III), or d) reducing carboxamides of the formula (VI) or (VI a) to the corresponding amines,

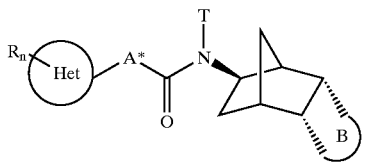

VI

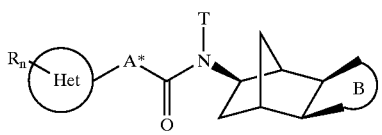

VI a wherein A* corresponds to a bond or $(C_1-C_3)$-alkyl and the other radicals are defined as described above, or e) alkylating compounds of the formula (I) or (I a) in which T corresponds to hydrogen, using alkylating agents of the formula (VII),

T*—U  VII wherein T* is $(C_1-C_4)$-alkyl and U has the meaning described above, so that tertiary amines result from this reaction;

or f) reacting a dicyclopentadienylplatinum complex of the formula (VIII)

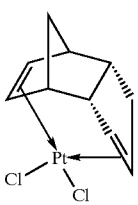

VIII with amines of the formula (IX),

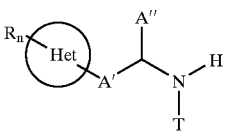

IX and subsequently reducing the intermediate formed to compounds of the formula (I) or (I a) (J. K. Stille and D. B. Fox, JACS 92:1274 (1970)), wherein T, $R_n$ and Het have the meanings indicated above; independently of one another, A' corresponds to a bond or $(C_1-C_3)$-alkyl and A" to H or $(C_1-C_3)$-alkyl; and A' and A", together with the carbon atom to which the nitrogen atom is bonded, represent as many carbon atoms as A represents in formula (I).

The compounds of formula (I) or (I a) may be optionally converted into the pharmaceutically tolerable salt or trifluoroacetate.

It has already been proposed that phenylalkyl-substituted norbornylamino derivatives are effective inhibitors of the sodium-proton exchanger, subtype 3 (NHE3). In this case, it appears that, of several stereoisomers, the compounds having an exo/endo-configuration octahydro-4,7-methanoinden-5-ylamine unit, wherein the nitrogen is exo and the five-membered ring is endo-fused, are active NHE3 inhibitors. Substances having an exo/exo-configuration octahydro-4,7-methanoinden-5-ylamine unit likewise showed marked NHE3-inhibiting action, while the corresponding endo/endo and endo/exo derivatives were markedly less active on the NHE3 (German published application 199 60 204 A1-HMR 99/L 073).

Surprisingly, it has now been found that the aromatic moiety of the phenylalkyl substituents can be substituted by heteroaromatic rings producing NHE3-inhibiting activity.

The relatively long-known inhibitors of the sodium/proton exchanger, subtype 3 disclosed in EP-A 825 178 (HOE 96/F226) represent relatively polar structures and correspond to the acylguanidine type of compounds (J.-R. Schwark et al. Eur. J. Physiol (1998) 436:797). In contrast, the compounds according to the invention are surprisingly lipophilic substances that are not of the acylguanidine type. See also the proposed compounds of the phenyalkyl norbornylamine type (DE 199 60 204.2-HMR 99/L 073). Squalamine and the above phenylalkyl norbornylamino derivatives are only the fourth substance class of NHE3 inhibitors known hitherto (M. Donowitz et al., Am. J. Physiol. 276 (Cell Physiol. 45): C136–C144). Additionally, squalamine does not achieve its maximum potency immediately, but only after approximately one hour. Compared with the above acylguanidines, the compounds of the invention are distinguished by their superior ability to cross the membrane and, compared with squalamine, by a more rapid onset of action.

NHE3 is found in the body of various species, mostly in the bile, the intestine, and in the kidney (Larry Fliegel et al., Biochem. Cell. Biol. 76: 735–741 (1998)), but can also be detected in the brain (E. Ma et al., Neuroscience 79: 591–603).

The compounds of the formula (I) or (I a) according to the invention are suitable for use as antihypertensives for the treatment of primary and secondary hypertension.

Moreover, these compounds, on their own or in combination with NHE inhibitors of other subtype specificity, can protect acutely or chronically oxygen-deficiently supplied organs by reducing or preventing ischemically induced damage. Thus, the compounds of the invention are suitable as pharmaceuticals, in the treatment of acute or chronic kidney failure and during surgical interventions such as in organ transplantation of the kidney and liver, where the compounds can be used both for the protection of the organs in the donor before and during removal and for the protection of removed organs, (for example during treatment with or storage in physiological bath fluids, and during transfer to the recipient's body). Ischemically induced damage to the intestine can also be avoided.

Corresponding to the protective action against ischemically induced damage, the compounds of the invention are also potentially suitable as pharmaceuticals for the treatment of ischemia of the nervous system, including the CNS, where they are suitable, for example, for the treatment of stroke or cerebral odema. Moreover, the compounds of the formula (I) or (I a) according to the invention are likewise suitable for the treatment of forms of shock, such as, for example, allergenic, cardiogenic, hypovolemic, and bacterial shock.

Furthermore, the compounds of the invention induce an improvement in the respiratory drive and are therefore used for the treatment of respiratory conditions in the following clinical conditions and diseases: disturbed central respiratory drive (e.g. central sleep apnea, sudden infant death, post operative hypoxia), muscular-related respiratory disorders, respiratory disorders after long-term ventilation, respiratory disorders during adaptation in a high mountain area, obstructive and mixed forms of sleep apnea, acute and chronic lung diseases with hypoxia and hypocapnia.

The compounds of the invention additionally increase the muscle tone of the upper airways, so that snoring is suppressed.

A combination of an NHE inhibitor with a carboanhydrase inhibitor, (e.g. acetazolamide) where the latter produces metabolic acidosis and thereby even increases the respiratory activity, proves to be advantageous as a result of increased activity and decreased use of active compound.

It has been shown that the compounds according to the invention have a mild laxative action and accordingly can be used advantageously as laxatives or, in the case of threatening intestinal blockage, for the prevention of ischemic damage that accompanies blockages in the intestinal region.

Furthermore, the use of the compounds of the formula (I) or (I a) according to the invention makes it possible to prevent gallstone formation.

The compounds of the formula (I) or (I a) according to the invention additionally show an action against ectoparasites.

Moreover, the compounds of the formula (I) or (I a) according to the invention can exert an inhibitory action on the proliferation of cells, for example fibroblast cell proliferation and the proliferation of the smooth vascular muscle cells. The compounds of the formula (I) or (I a) are therefore suitable as valuable therapeutics for diseases in which cell proliferation is a primary or secondary cause, and can therefore be used as antiatherosclerotics, as agents against diabetic late complications, cancers, fibrotic disorders (such as, for example, pulmonary fibrosis, liver fibrosis, or kidney fibrosis), endothelial dysfunction, and organ hypotrophy and hyperplasia, such as, for example, prostate hyperplasia or prostate hypertrophy.

The compounds according to the invention are effective inhibitors of the cellular sodium/proton antiporter, which is raised in numerous disorders (essential hypertension, atherosclerosis, diabetes etc.) even in those cells that are easily accessible to measurement, such as, for example, erythrocytes, platelets or leukocytes. The compounds according to the invention are therefore suitable as outstanding and simple scientific tools, for example in their use as diagnostics for the determination and differentiation of certain forms of hypertension, athererosclerosis, diabetes, proliferative disorders, etc. Moreover, the compounds of the formula (I) or (I a) are suitable for preventive therapy to prevent the development of high blood pressure, for example of essential hypertension.

It has moreover been found that NHE inhibitors exhibit a favorable influence on the serum lipoproteins. It is generally recognized that for the formation of artereosclerotic vascular changes, for example in coronary heart disease, excessively high blood lipid values, 'hyperlipoprotanemias', are an important risk factor. The lowering of increased serum lipoproteins is therefore of extreme importance for the prophylaxis and the regression of atherosclerotic changes. The compounds according to the invention can therefore be used for the prophylaxis and regression of atherosclerotic changes by excluding a causal risk factor. With this protection of the vessels against the syndrome of endothelial dysfunction, compounds of the formula (I) or (I a) are valuable pharmaceuticals for the prevention and treatment of coronary vascular spasms, athereogenesis and atheroesclerosis, left-ventricular hypertrophy and dilated cardiomyopathy, and thrombotic disorders.

The compounds mentioned are therefore advantageously used for the production of a medicament for the prevention and treatment of sleep apneas and muscular-related respiratory disorders; for the production of a medicament for the prevention and treatment of snoring, for the production of a medicament for lowering the blood pressure, for the production of a medicament having laxative action for the prevention and treatment of intestinal blockages; for the production of a medicament for the prevention and treatment of disorders that are induced by ischemia and reperfusion of central and peripheral organs, such as acute kidney failure, stroke, endogenous states of shock, intestinal disorders, etc; for the production of a medicament for the treatment of hypercholesterolemia; for the production of a medicament for the prevention of atherogenesis and of athereosclerosis; for the production of a medicament for the prevention and treatment of diseases which are induced by raised cholesterol levels; for the production of a medicament for the prevention and treatment of diseases which are induced by endothelial dysfunction; for the production of a medicament for the treatment of attack by ectoparasites; for the production of a medicament for the treatment of the diseases mentioned in combination with blood pressure-lowering substances, for example angiotensin-converting enzyme (ACE) inhibitors and angiotensin receptor antagonists. A combination of an NHE inhibitor of the formula (I) or (I a) with an active compound lowering the blood lipid level, such as an HMG-CoA reductase inhibitor (e.g. Lovastatin or Pravastatin) proves to be a favorable combination having intensified action and decreased use of active substance. In this case, the HMG-CoA reductase inhibitor produces a hypolipodemic effect and thereby increases the hypolipodemic properties of the NHE inhibitor of the formula (I) or (I a).

The administration of sodium/proton exchange inhibitors of the formula (I) or (I a) as novel pharmaceuticals for lowering raised blood lipid levels, and the combination of sodium/proton exchange inhibitors with pharmaceuticals having a blood pressure-lowering and/or hypolipodemic action is claimed.

Pharmaceuticals containing a compound of formula (I) or (I a) can be administered orally, parenterally, intravenously, rectally, or by inhalation. The method of administration depends on the particular clinical picture of the disorder. The compounds (I) or (I a) can be used on their own or together with pharmaceutical excipients, namely both in veterinary and in human medicine.

The person skilled in the art is familiar on the basis of his/her expert knowledge with excipients that are suitable for the desired pharmaceutical formulation. In addition to solvents, gel formers, suppository bases, tablet excipients, and other active compound carriers, it is possible to use, for example, antioxidants, dispersants, emulsifiers, antifoams, flavor corregents, preservatives, solubilizers, and/or colorants.

For a form suitable for oral administration, the active compounds are mixed with the additives suitable therefor, including excipients, stabilizers, or inert diluents, and brought by means of the customary methods into the suitable administration forms, including tablets, coated tablets, hard gelatin capsules, aqueous, alcoholic, or oily solutions. Inert carriers that can be used include, for example, gum arabic, magnesia, magnesium carbonates, potassium phosphates, lactose, glucose, starch, or cornstarch. Preparation can be carried out either as dry or as moist granules. Possible oily excipients or solvents include, for example, vegetable or animal oils, such as, for example, sunflower oil or cod-liver oils.

For subcutaneous or intravenous administration, the active compounds are brought into solution, suspension, or emulsion, if desired with the substances customary therefor such as, for example, solubilizers, emulsifiers, or further excipients. Suitable solvents include, for example, water, physiological saline solution, or alcohols (e.g. ethanol, propanol, glycerol), and sugar solutions such, for example, as glucose or mannitol solutions, or alternatively a mixture of the different solvents mentioned.

Pharmaceutical formulations suitable for administration in the form of aerosols or sprays include, for example, solutions, suspensions, or emulsions of the active compound of the formula (I) or (I a) in a pharmaceutically innocuous solvent, such as, ethanol or water, or a mixture of such solvents.

If required, the formulation can also contain other pharmaceutical excipients such as, for example, surfactants, emulsifiers and stabilizers, and a propellant. Such a preparation may contain the active compound in a concentration of approximately 0.1 to 10% by weight, and sometimes approximately 0.3 to 3% by weight.

The dose of the active compound of the formula (I) or (Ia) to be administered and the frequency of administration depend on the potency and duration of action of the compounds used; on the nature and severity of the disease to be treated; and on the sex, age, weight, and individual responsiveness of the mammal to be treated.

On average, the daily dose of a compound of the formula (I) or (Ia) in the case of a patient weighing approximately 75 kg may be at least 0.001 mg/kg, sometimes 1–10 mg/kg, and at most 100 mg/kg, of bodyweight. In acute episodes of the diseases, even higher and more frequent doses may also be necessary, e.g. up to 4 individual doses per day, for instance in the case of i.v. administration, for example in the case of an infarct patient in the intensive care unit, up to 200 mg per day may be necessary.

Experimental Section

Abbreviations used:

| | | | |
|---|---|---|---|
| CI | chemical ionization | bp | boiling point |
| DIP | diisopropyl ether | MgSO$_4$ | magnesium sulfate |
| EA | ethyl acetate | m.p. | melting point |
| ES | electrospray | MS | mass spectrum |
| FAB | fast atom bombardment | NaOH | sodium hydroxide solution |
| h | hours | RP | reversed phase |
| HCl | hydrochloric acid | THF | tetrahydrofuran |
| HPLC-RT | HPLC retention time | TFA | trifluoroacetic acid |

EXAMPLES:

If not described otherwise, the examples mentioned here are racemates.

The HPLC or LCMS conditions used for characterization were as follows: HPLC and HPLC-MSD systems from Agilent Technologies of the series 1100 with DAD detector, Merck Purospher column (3 μ, 2×55 mm), column temperature: 30° C., wavelength: 220 nm, flow: 0.5 ml/min, gradient; from 95% water (0.05% TFA)/5% acetonitrile in 4 min to 5% water (0.05% TFA)/95% acetonitrile, then the column was kept at 5% water (0.05% TFA)/95% acetonitrile for 1.5 min.

The values marked by * were determined under the following conditions: HPLC-MSD system from Agilent Technologies of the series 1100 with DAD detector, Nucleosil column (C-18, 5μ, 4×125 mm), column temperature: 40° C., wavelength: 220 nm, flow: 0.65 ml/min, gradient: 95% water [water/acetonitrile 9:1 with 0.1% TFA]/5% acetonitrile [water/acetonitrile 1:9 with 0.1% TFA] for 2 min, then to 5% water/95% acetonitrile in 10 min, then the column was kept at 5% water/95% acetonitrile for 5 min.

For the characterization of the final compounds, the HPLC retention time and the result of the mass-spectroscopic investigation, which was carried out separately, are given.

Example 1

(rac)-exo/endo-(octahydro-4,7-methanoinden-5-yl) pyridin-3-ylmethylamine Hydrochloride

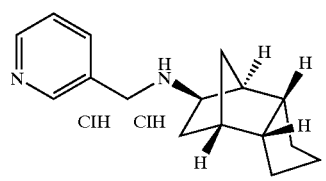

a) exo/endo-3a,4,5,6,7,7a-hexahydro-1H-4,7-methanoinden-5-ylamine and exo/endo-(3a,4,5,6,7,7a-hexahydro-3H-4,7-methanoinden-5-yl)-pyridin-3-ylmethylamine 10 g of exo-5-isothiocyanate-5,6-dihydroenedodicyclo-pentadiene (Maybridge international) were dissolved in 61 ml of formic acid and the solution was boiled under reflux for 45 hours. After cooling, a black precipitate was filtered off and the filtrate was concentrated. The residue was diluted with water, and 10 g of sodium hydroxide were slowly added in the presence of heat. The mixture was then cooled to room temperature, extracted three times with toluene. The combined organic phases were dried using $MgSO_4$, the $MgSO_4$ was filtered off and the filtrate was concentrated. The residue was distilled and afforded 3.38 g of a clear oil.

HPLC-RT=3.15 min; MS (Cl+): 150 (M+H)$^+$ b) (exo/endo)-octahydro-4,7-methanoinden-5-ylamine 3.3 g of the double-bond isomer mixture from 1a) were dissolved in 30 ml of methanol. 0.5 g of palladium on carbon (10%), as catalyst, was added thereto and the mixture was hydrogenated under a hydrogen atmosphere for 4 h. The catalyst was then filtered off, washed with methanol and the filtrate was concentrated. After drying under a high vacuum, 3 g of product were obtained as a clear oil.

HPLC-RT=3.33 min; MS (ES+): 152 (M+H)$^+$ c) exo/endo-(octahydro-4,7-methanoinden-5-yl)pyridin-3-ylmethylamine Hydrochloride A solution of 3 g of the exo/endo-configuration octahydro-4,7-methanoinden-5-ylamine from 1 b) and 2.15 g of pyridin-3-carbaldehyde in 200 ml of toluene were heated to boiling for 5 hours in a water separator after addition of a catalytic amount of p-toluenesulfonic acid., After allowing to stand overnight at room temperature, the solvent was distilled off. The residue was dissolved in 150 ml of methanol and 0.91 g of sodium borohydride were then added in small portions to the ice-cooled solution with stirring. The mixture was stirred at room temperature for several hours and then rendered strongly acidic using excess methanolic HCl. After concentrating in a rotary evaporator, the residue was dissolved in water and rendered alkaline using potassium carbonate solution. The mixture was then extracted three times with EA, and the combined extracts were dried over magnesium sulfate, filtered, and adjusted to pH 1–2 using ethereal HCl. The solvent was then decanted off from the precipitated product and the residue was dissolved in ethanol in the warm. After cooling, the product was precipitated using ether. 2.85 g of pale crystals were obtained.

HPLC-RT=3,15, MS (ES+): 243.2 (M+H)$^+$

Example 2

(+)-exo/endo-(octahydro-4,7-methanoinden-5-yl)-pyridin-3-ylmethylamine Hydrochloride

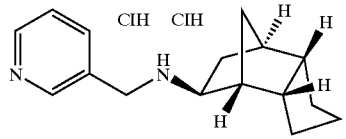

a) (+)-(exo/endo)-octahydro-4,7-methanoinden-5-ylamine and (−)-(exo/endo)-octahydro-4,7-methanoinden-5-ylamine The title compounds can be obtained enantiomerically pure starting from racemic (exo/endo)-octahydro-4,7-methanoinden-5-ylamine from Example 1 b) either by means of chromatography on chiral columns or by crystallization using chiral acids. Using Z-valine, for example, (+)-(exo/endo)-octahydro-4,7-methanoinden-5-ylamine can be obtained as follows:

a1) (+)-(exo/endo)-octahydro-4,7-methanoinden-5-ylamine by resolution using Z-valine A mixture of 50 g of racemic (exo/endo)-octahydro-4,7-methanoinden-5-ylamine from Example 1b) and 83.2 g of Z-valine in 1.5 l of tetrahydrofuran was heated to boiling. The clear solution was allowed to cool to ambient temperature in the course of 3 hours. It was then stirred at ambient temperature for a further 20 hours. The precipitate was filtered off with suction, washed with 50 ml of tetrahydrofuran, and dried at 40° C. in a drying oven. 55 g of the salt of 65% diastereomeric purity were obtained. After recrystallizing three times from one liter of tetrahydrofuran in each case, 30 g of the salt of >95% diastereomeric purity were obtained.

1 N sodium hydroxide solution was added to a suspension of 9.4 g of the above Z-valine salt in 30 ml of toluene and water until the pH remained constant at 11. In the course of this, the solid went into solution. The phases were separated and the water phase was extracted a further three times using 10 ml of toluene in each case. The combined toluene phases were dried over sodium sulfate, and the toluene was distilled off in vacuo.

It was possible to react the amine thus obtained (3.3 g, enantiomeric purity >95%) without further purification.

a2) (−)-(exo/endo)-octahydro-4,7-methanoinden-5-ylamine by resolution using Z-D-valine:

The (−) enantiomer was obtained analogously to the above procedure using Z-D-valine. Thus, starting from 500 mg of (+)-(exo/endo)-octahydro-4,7-methanoinden-5-ylamine from Example 1b), after precipitation and two recrystallizations, it was possible to obtain 468 mg of the salt having a diasteromeric purity of >95%.

b) (+)-exo/endo-(octahydro-4,7-methanoinden-5-yl)-pyridin-3-ylmethylamine hydrochloride A solution of 1.4 g of the (+)-exo/endo-configuration octahydro-4,7-methanoindene-5-ylamine from 2a1) and 1 g of pyridin-3-carbaldehyde in 100 ml of toluene was heated to boiling for 5 hours in a water separator after addition of a catalytic amount of p-toluenesulconic acid. After allowing the solution to stand overnight at room temperature the solvent was distilled off. The residue was dissolved in 75 ml of methanol and 0.42 g of sodium borohydride were then added in small portions to the ice-cooled solution. The mixture was stirred for several hours at room temperature, allowed to stand overnight and then rendered strongly acidic using excess methanolic HCl. The crystallization initiated by trituration was completed overnight in a refrigerator. After decanting off the solution, the residue was taken up with aqueous potassium carbonate solution and extracted three times with EA at pH 11, and the combined extracts were dried over magnesium sulfate, filtered, and adjusted to pH 1–2 using methanolic HCl. The product was then precipitated by addition of ether. 1.1 g of pale crystals were obtained.

HPLC-RT=3.20; MS (Cl+): 243.3 (M+H)$^+$; $[\alpha]_{Na\ 589\ nm}$: +34,6° in ethanol

Example 3

(−)-exo/endo-(octahydro4,7-methanoinden-5-yl)pyridin-3-ylmethylamine Hydrochloride

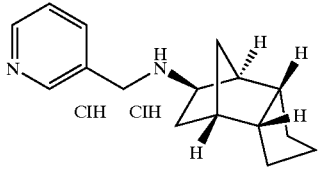

A solution of 1.4 g of (−)-exo/endo-configuration octahydro-4,7-methanoinden-5-ylamine from 2a2) and 1 g of pyridin-3-carbaldehyde in 100 ml of toluene were heated to boiling for 5 hours in a water separator after addition of a catalytic amount of p-toluenesulfonic acid. The solvent was distilled off after allowing the solution to stand overnight at room temperature. The residue was dissolved in 75 ml of methanol and 0.42 g of sodium borohydride was then added in small portions with stirring to the ice-cooled solution. The mixture was stirred for several hours at room temperature, allowed to stand overnight and was then rendered strongly acidic using excess methanolic HCl. The crystallization initiated by trituration was completed overnight in a refrigerator. After decanting off the solution, the residue was taken up with aqueous potassium carbonate solution and extracted three times with EA at pH 11, and the combined extracts were dried over magnesium sulfate, filtered and adjusted to pH 1–2 using methanolic HCl. The product was then precipitated by addition of ether. 1.1 g of pale crystals were obtained.

HPLC-RT=3.12; MS (Cl+): 243.3 (M+H)+; [□]Na 589 nm:−32,5° in ethanol

Example 4 exo/endo-furan-2-ylmethyl-(octahydro-4,7-methanoinden-5)-amine Hydrochloride

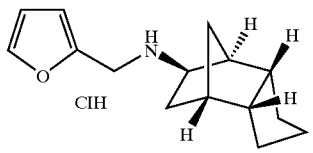

200 mg of the exo/endo-configuration octahydro-4,7-methanoinden-5-ylamines from Example 1 b), 127 mg of 2-furaldehyde, and 101 mg of p-toluenesulfonic acid were dissolved in 20 ml of toluene (anhydrous) and the solution was boiled under reflux for 4 hours. After allowing the solution to stand overnight at room temperature, the solvent was distilled off. The residue was dissolved in 15 ml of methanol and 0.6 g of sodium borohydride were then added to the ice-cooled solution in small portions with stirring. The mixture was stirred for several hours at room temperature and then rendered acidic using excess methanolic HCl. After concentrating in a rotary evaporator, the residue was taken up in 2 N NaOH and extracted three times with EA. The combined organic phases were acidified using methanolic HCl and concentrated. The oily residue was purified by means of preparative HPLC on RP-18 using acetonitrile/water (0.05% TFA). The clean fractions were combined, the acetonitrile was removed in a rotary evaporator, and the mixture was adjusted to pH 11 using potassium carbonate and extracted with EA. The combined EA phases were dried using MgSO₄ and concentrated after filtering off the MgSO₄. The residue was taken up with 2 N hydrochloric acid and freeze-dried. 119 mg of the hydrochloride were obtained as a white solid.

HPLC-RT=3.60 min; MS (ES+):232.2 (M+H)+

Example 5 exo/endo-(octahydro-4,7-methanoinden-5-yl)-thiophen-2-ylmethylamine Hydrochloride

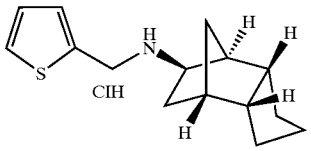

200 mg of exo/endo-configuration octahydro-4,7-methanoinden-5-ylamine from Example 1b), 148 mg of thiophene-2-aldehyde and 101 mg of p-toluenesulfonic acid were dissolved in 20 ml of toluene (anhydrous) and the solution was boiled under reflux for 4 hours. After allowing the solution to stand overnight at room temperature, the solvent was distilled off. The residue was dissolved in 15 ml of methanol and 0.06 g of sodium borohydride were then added to the ice-cooled solution in small portions with stirring. The mixture was stirred for several hours at room temperature and was then rendered acidic using excess methanolic HCl. After concentrating in a rotary evaporator, the residue was taken up in 2 N NaOH and extracted three times with EA. The combined organic phases were acidified with methanolic HCl and concentrated. The oily residue was purified by means of preparative HPLC on RP-18 using acetonitrile/water (0.05% TFA). The clean fractions were combined, acetonitrile was removed in a rotary evaporator, and the mixture was adjusted to pH 11 using potassium carbonate and extracted with EA. The combined EA phases were dried using MgSO₄ and concentrated after filtering off the MgSO₄. The residue was taken up with 2 N hydrochloric acid and freeze-dried. 61 mg of the hydrochloride were obtained as a white solid.

HPLC-RT=3.84 min; MS (Cl+):248.3 (M+H)+

Example 6 exo/exo-(octahydro-4,7-methanoinden-5-yl)-pyridin-3-ylmethylamine Hydrochloride

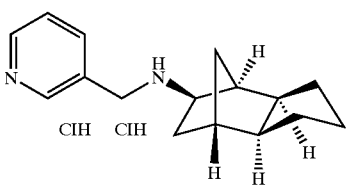

a) Octahydro-4,7-methano-inden-5-ole 25 g of tricyclo[5.2.1.0 (2,6)]decan-8-one (Aldrich) were dissolved in 100 ml of methanol and treated with 6.3 g of solid sodium borohydride at room temperature with slight cooling and stirring in portions in the course of 2 h. The mixture was then stirred for 2 h and allowed to stand overnight. About 40 ml of 2 N HCl were then added dropwise with cooling, followed by 20 ml of water. The mixture was concentrated, the residue was treated with ethyl acetate, and the ethyl acetate phase was washed once with water and once with sodium hydrogen carbonate solution. After drying using magnesium sulfate, the ethylacetate phase was filtered and concentrated. 26 g of oil remained, which was purified by vacuum distillation. 20.7 g of an oily liquid were obtained (bp$_{0.5}$ 76° C.).

HPLC-RT=4.55 min; MS (Cl+):134.8 (M-OH)$^+$ b) 2-(Octahydro-4,7-methanoinden-5-yl)-isoindole-1,3-dione 1.7 g of diethyl azodicarboxylate diluted with 5 ml of THF were added with stirring to a solution of 1.66 g of octahydro-4,7-methanoinden-5-ole from 6 a), 1.47 g of phthalimide and 2.62 g of triphenylphosphine in 15 ml of THF. After standing overnight, the reaction mixture was evaporated, the residue was stirred with ether, the precipitate was filtered off with suction, and the filtrate was concentrated. The residue was purified on silica gel/toluene. 1.36 g of a yellow oil were obtained.

HPLC-RT=5.82 min; MS (Cl+):282.2 (M+H)$^+$ c) exo/exo-octahydro-4,7-methanoinden-5-ylamine 0.4 g of hydrazine hydrate was added dropwise to a solution of 1.12 g of 2-(octahydro-4,7-methanoinden-5-yl)-isoindole-1,3-dione from 6 b) and 15 ml of ethanol and stirred at 65° C. for 2 h. The mixture was then adjusted to pH 1–2 using conc. HCl and treated with 10 ml of ethanol. The precipitate was filtered off and the filtrate was concentrated. The residue was purified by means of preparative HPLC on RP-18 using acetonitrile/water (0.05% trifluoroacetic acid). After freeze-drying, 567 mg of product were obtained as trifluoroacetate. Treatment with sodium hydroxide solution and ethyl acetate yielded 322 mg of the free amine.

HPLC-RT=3.47 min; MS (Cl+):152.0 (M+H)$^+$ d) exo/exo-(octahydro-4,7-methanoinden-5-yl)-pyridin-3-ylmethylamine hydrochloride A solution of 332 mg of the exo/exo-configuration octahydro-4,7-methano-indenylamine from 6 c) and 215 mg of pyridin-3-carbaldehyde in 20 ml of toluene were heated to reflux for 5 hours after addition of a catalytic amount of p-toluenesulfonic acid. After allowing the solution to stand overnight at room temperature the solvent was distilled off. The residue was dissolved in 15 ml of methanol and 91 mg of sodium borohydride were then added in small portions to the cooled solution with stirring. The mixture was stirred at room temperature for several hours and then rendered strongly acidic using excess methanolic HCl. After concentrating in a rotary evaporator, the residue was taken up with 2 N sodium hydroxide solution. After extracting three times with EA, the combined extracts were concentrated, and the residue was purified by means of preparative HPLC on RP-18 using acetonitrile/water (0.05% TFA). The product-containing fractions were combined, freeze-dried, and again purified by HPLC. The clean fractions were combined, the acetonitrile was removed on a rotary evaporator, and the residue was adjusted to pH 11 using potassium carbonate and extracted with EA. The combined EA phases were dried using MgSO$_4$ and concentrated after filtering off the MgSO$_4$. The residue was taken up with 2 N hydrochloric acid and freeze-dried. 35 mg of the hydrochloride were obtained as a white solid.

HPLC-RT=3.25 min, MS (ES+):243.1 (M+H)$^+$

Example 7 exo/endo-(3-chloro-5-trifluoromethylpyridin-2-ylmethyl) (octahydro-4,7-methanoinden-5-yl)-amine Trifluoroacetic Acid Salt

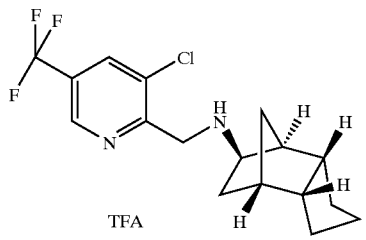

0.5 mmol of exo/endo-octahydro-4,7-methanoindene-5-ylamine from Example 1 b), 0.5 mmol of 3-chloro-5-trifluoromethylpyridin-2-carbaldehyde, 140 µl of triethylamine, and 10 ml of dichloromethane were introduced, 250 µl of a 1-molar solution of titanium tetrachloride in toluene were added dropwise and the mixture was stirred at room temperature for 24 h. 1.5 ml of a 1-molar solution of sodium cyanoborohydride in THF were then slowly added and the mixture was stirred at room temperature for 30 min. The mixture was then treated with 15 ml of 2 N NaOH and stirred for 15 min. The solid was filtered off and washed with water. 30 ml of EA were added to the filtrate, the mixture was shaken and then the organic phase was separated off. After drying, the mixture was concentrated and the residue was purified by means of preparative HPLC (RP18, gradient acetonitrile/water 30%->90%, with 0.1% TFA in both components). After freeze-drying, 4.7 mg were obtained as a white solid.

HPLC-RT=11.23 min*, MS (ES+):345.2 (M+H)$^+$

Example 8 exo/endo-(decahydro-1,4-methanonaphthalen-2-yl)-pyridin-3-ylmethyl-amine Hydrochloride

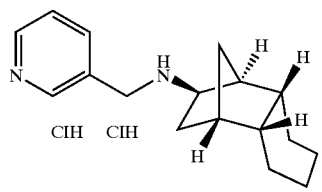

a) bis-(3-chloro-1,2,3,4-tetrahydro-1,4-methanonaphthalen-2-yl)-diazene N,N'-dioxide 3.34 g of isoamyl nitrite were added to a solution of 3.56 g of benzonorbornadiene [L. Friedman and F. M. Logullo, J. Org. Chem. 34: 3089–3092, (1969)] in 6 ml of glacial acetic acid and 6 ml of ethanol. 8.5 ml of a 15% strength solution of hydrogen chloride gas in ethanol were then added dropwise. The resulting suspension was stirred at room temperature for a further 2½ hours and then treated with 20 mg of diisopropyl ether. The solid was filtered off after further stirring for 30 minutes. A pale crystalline solid; m.p. 187–188° C., was obtained.

MS (FAB):415.1 (M+H)$^+$ b) (exo)-1,2,3,4-tetrahydro-1,4-methanonaphthalen-2-ylamine 3 g of bis-(3-chloro-1,2,3,4-tetrahydro-1,4-methanonaphthalen-2-yl)-diazene N,N'-dioxide were suspended in 150 ml of methanol and hydrogenated in an autoclave with hydrogen at 100 bar and 100° C. for 20 hours using Raney nickel catalyst. After filtering off the catalyst, the solvent was evaporated. The residue was treated with water, rendered strongly alkaline with NaOH, and extracted repeatedly with methyl tert-butyl ether. After drying the organic phases, the desired amine was obtained as a pale yellow liquid.

MS (ES+):160.0 (M+H)$^+$ c) exo/endo-decahydro-1,4-methanonaphthalen-2-ylamine

A solution of 1 g of exo/endo-1,2,3,4-tetrahydro-1,4-methanonaphthalen-2-ylamine in 10 ml of methanol and 30 ml of 2 N hydrochloric acid was hydrogenated in an autoclave with hydrogen at 100 bar and 90° C. for 10 hours using 0.4 g of RuO$_2$. After separating off the catalyst, the solution was evaporated to half the original volume. The aqueous solution thus obtained was rendered strongly alkaline with 10 N NaOH and extracted repeatedly with methyl tert-butyl ether. After drying and evaporating the solvents, exo/endo-decahydro-1,4-methanonaphthalen-2-ylamine was obtained as a colorless oil, which was stored under argon.

MS (Cl+):166.2 (M+H)$^+$ d) exo/endo-(decahydro-1,4-methanonaphthalen-2-yl)-pyridin-3-ylmethyl-amine hydrochloride A solution of 0.71 g of pyridin-3-aldehyde and 1.1 g of exo/endo-decahydro-1,4-methanonaphthalene-2-ylamine in 40 ml of toluene was boiled under reflux for 4 hours after addition of a small catalytic amount of p-toluenesulfonic acid (3–5 mg) and the solvent was then distilled off. After dissolving the oily residue in about 30 ml of anhydrous methanol, the solution was treated in portions with 0.335 g of sodium borohydride with cooling and stirring, stirred at room temperature for a further 2 hours, and allowed to stand overnight. The solution was then rendered acidic using a solution of HCl in methanol, the precipitate was filtered off, and the solvent was evaporated. The residue was recrystallized from ethanol, m.p. 283–285° C.

HPLC-RT=3.38 min, MS (Cl+):257.4 (M+H)$^+$

The compounds described below were prepared from carbonyl derivatives known from the literature and the appropriate amines, analogously to the example indicated:

TABLE 1

| Example | | Salt | Analogously to Example | MS | HPLC RT [min] |
|---|---|---|---|---|---|
| 9 | | HCl | 5 | ES+ 232.2 (M + H)+ | 3.73 |
| 10 | | HCl | 5 | ES+ 260.2 (M + H)+ | 4.00 |
| 11 | | HCl | 5 | Cl+ 248.0 (M + H)+ | 3.88 |
| 12 | | HCl | 5 | ES+ 243.1 (M + H)+ | 3.63 |
| 13 | | HCl | 5 | Cl+ 243.0 (M + H)+ | 3.14 |

TABLE 1-continued

| Example | | Salt | Analogously to Example | MS | HPLC RT [min] |
|---|---|---|---|---|---|
| 14 | (structure) | HCl | 5 | CI+ 232.2 (M + H)+ | 3.05 |
| 15 | (structure) | HCl | 5 | CI+ 232.1 (M + H)+ | 3.05 |
| 16 | (structure) | HCl | 5 | ES+ 231.2 (M + H)+ | 3.76 |
| 17 | (structure) | HCl | 5 | ES+ 249.1 (M + H)+ | 3.47 |
| 18 (racemate) | (structure) | HCl | 5 | CI+ 244.1 (M + H)+ | 3.39 |
| 19 (+) | (structure) | HCl | 2 | CI+ 244.2 (M + H)+ | 3.41 |
| 20 (−) | (structure) | HCl | 3 | CI+ 244.2 (M + H)+ | 3.40 |
| 21 | (structure) | HCl | 8 | ES+ 258.1 (M + H)+ | 3.65 |

TABLE 1-continued

| Example | | Salt | Analogously to Example | MS | HPLC RT [min] |
|---|---|---|---|---|---|
| 22 | (pyrimidin-5-ylmethyl-amino bicyclic structure) | HCl | 5 | ES+ 244.1 (M + H)+ | 3.33 |
| 23 | (pyridazin-4-ylmethyl-amino bicyclic structure) | HCl | 5 | ES+ 244.2 (M + H)+ | 3.43 |
| 24 | (1H-pyrazol-3-ylmethyl-amino bicyclic structure) | HCl | 5 | Cl+ 232.1 (M + H)+ | 3.42 |
| 25 | (pyridin-3-ylmethyl-amino bicyclic structure) mixture (pyridin-3-ylmethyl-amino bicyclic structure with alkene) | HCl | 5 | Cl+ 241.2 (M + H)+ | 3.07 |
| 26 | (2,5-dichlorothiophene-ethyl-amino bicyclic structure) | TFA | 7 | ES+ 330.1 (M + H)+ | 11.78* |
| 27 | (pyrazol-1-yl-propyl-amino bicyclic structure) | TFA | 7 | ES+ 274.2 (M + H)+ | 9.75* |

TABLE 1-continued

| Example | | Salt | Analogously to Example | MS | HPLC RT [min] |
|---------|---|------|------------------------|-----|---------------|
| 28 | [structure] | TFA | 7 | ES+ 293.1 (M + H)+ | 10.03* |
| 29 | [structure] | TFA | 7 | ES+ 356.3 (M + H)+ | 11.18* |
| 30 | [structure] | TFA | 7 | ES+ 319.3 (M + H)+ | 9.99* |

Pharmacological Data

Example 31

Description of the Caco 2 Model

The Caco-2 cell line was acquired from the American Type Culture Collection (ATCC) and maintained in Dulbecco's Modified Eagle medium (high glucose content), supplemented with nonessential amino acids, L-glutamine, penicillin/streptomycin, and 10% strength fetal calf serum. The Caco-2 cell line was then kept in an incubator under a 10% strength $CO_2$ atmosphere at 95% strength relative humidity and 37° C. The cells were grown in cell culture flasks (175 cm$^2$). For the transport investigations, the Caco-2 cells were inoculated into polycarbonate cell culture inserts (costar Transwells®, pore size: 3 μm, area: 4.71 cm$^2$) at a cell density of 6.5×10$^4$ cells/cm$^2$ and incubated in six-well culture plates with a change of medium after 4 and 8 days and then every second day thereafter. 21 to 25 day-old monolayers were used for the experiments.

In each test series, a 21 day-old monolayer was tested for its properties with $^3$H-dextran as a permeability marker. The value of the transfer rate (cumulative) had to be in the range of 2% after 120 min.

After eliminating the growth medium from the apical and the basolateral side, the monolayers were rinsed with the transport buffer (Hank's balanced salt solution, pH 7.8; containing 2.8 g/l glucose).The cells were then equilibrated for 15 min at 37° C. under a 10% strength C02 atmosphere. The HBSS buffer was then removed. The test compounds were dissolved in a mixture of HBSS buffer and DMSO and added to the apical buffer such that a 1% strength (v/v) DMSO solution resulted. The test concentration in the first experiment was 1 mM, and 100 μM in the second. The experiments were carried out at 37° C. and started by the addition of 1.5 ml of test solution to the donor side (apical).

Transport buffer without compound was added to the recipient side (basolateral, 2.5 ml). At various points in time, samples were taken from the basolateral side (1 ml) and replaced by fresh buffer solution at 37° C. Apical samples were taken at the start and at the end (120 min) in order to determine the recovery rate of the compounds by means of these concentrations and the cumulative basolateral concentration.

The compounds were analyzed by means of HPLC.

The apparent permeability coefficient ($P_{app}$) was calculated by means of the following equation:

$$P_{app} = \frac{d_c \cdot V}{d_t \cdot A \cdot c_0},$$

wherein $d_c/d_t$ is the flow through the monolayer (μg of compound/ml x s), V is the liquid volume in the collection chamber (ml), A is the surface area size of the monolayer (cm$^2$) and $c_0$ is the initial concentration (μg of compound/ml) in the donor chamber. The flow through the monolayer was calculated from the cumulative basolateral concentration at the appropriate point in time with the aid of the initially linear data curve (linear up to 60 min). The respective determinations were made in triplicate, such that the calculated $P_{app}$ value represents the mean of three measurements. $P_{app}$ values of selected compounds were correlated with absorption values known from the literature and afforded a sigmoidal calibration curve. According to investigations by Artusson (Artursson P. and Karlsson J.; Biochem. Biophys. Res. Comm.,175 (3): 880–885 (1991)), a conclusion about the absorbed fraction of a compound can be made with the aid of this curve.

TABLE 2

Results:

| | | Absorbed fraction [%] |
|---|---|---|
| Example 1 | (pyridin-3-ylmethyl aminonorbornane · 2 HCl structure) | 100 |
| Example 18 | (pyrazin-2-ylmethyl aminonorbornane structure) | 100 |
| S 3226 | (bis-acylguanidine structure · 2 HCl) | <5 |
| S 2120 | (bis-acylguanidine structure · 2 HCl) | <1 |

Compared with the NHE3 active compounds of the acylguanidine type known from the literature (J.-R. Schwark et al. Eur. J. Physiol., 436:797 (1998)), the compounds of the formula (I) or (I a) show a clearly superior ability to cross the membrane.

Example 32

Description of the NHE Activity Measurements

Most of the molecular biology techniques follow protocols from the works "Current Protocols in Molecular Biology" (Ausubel, F. M., Brent, R., Kingston, R. E., Moore, D. D., Seidman, J. G., Smith, J. A. and Struhl, K., eds., John Wiley & Sons) and "Molecular Cloning: A Laboratory Manual" (Sambrock, J., Fritsch, E. F., and Maniatis, T., Cold Spring Harbor Laboratory Press (1989)).

In the context of our studies, stably transfected cell lines were produced that in each case expressed one of the following NHE subtypes: Human NHE1 (Sardet et al. Cell 56:271–280 (1989)), rabbit NHE2 (Tse et al.; J. Biol. Chem. 268:11917–11924 (1993)), human NHE3 (Brant et al. Am. J. Physiol. 269 (Cell Physiol. 38) C198–C206 (1995)), or rat NHE3 (Orlowski et al.; J. Biol. Chem. 267:9331–9339 (1992)).

The cDNA clones of the respective NHE subtypes obtained by Prof. Pouyssegur were, after addition of suitable linker sequences, cloned into the expression plasmid pMAMneo (obtainable, for example, via CLONTECH, Heidelberg) such that the recognition sequence for the restriction endonuclease NheI of the plasmid was approximately 20–100 Basepairs before the start codon of the respective NHE subtype and that the total coding sequence was present in the construct. In the case of the human NHE3 obtained from human kidney mRNA by means of RT-PCR, the RT-PCR primers were selected such that the cDNA band obtained had cleavage sites suitable for pMAMneo at its ends.

Using the "calcium phosphate method" (described in chapter 9.1 of "Current Protocols in Molecular Biology"), the NHE-deficient cell line LAP1 (Franchi et al.; Proc. Natl. Acad. Sci. USA 83:9388–9392 (1986)) was transfected with the plasmids that received the respective coding sequences of the NHE subtypes. After selection for transfected cells by means of growth in G418-containing medium (only cells which have obtained a neogene by transfection can survive under these conditions), selection was made for functional NHE expression. For this, the "Acid Load" technique described by Sardet was used (Sardet et al.; Cell 56:271–280 (1989)). Unlike untransfected LAP1 cells, cells that express a functional NHE subtype can also compensate for the acidification carried out in this test in the absence of $CO_2$ and $HCO_3$. After repetition of the "Acid Load" selection several times, the surviving cells were inoculated into microtiter plates such that one cell per well should occur statistically. Under the microscope, after approximately 10 days, a check was made to estimate how many colonies were growing per well. Cell populations from individual colonies were then investigated using the XTT proliferation kit (Boehringer Mannheim) with respect to their survival ability after "Acid Load". The best cell lines were used for further tests and, to avoid a loss of the transfected sequence, cultured in G418-containing medium under continuous selection pressure.

To determine $IC_{50}$ values for the inhibition of the individual NHE subtypes by specific substances, a test developed by S. Faber (Faber et al.; Cell. Physiol. Biochem. 6:39–49 (1996)), which is based on the "Acid Load" technique, was slightly modified.

In this test, the recovery of the intracellular pH ($pH_i$) after an acidification, which in the case of functional NHE occurs even under bicarbonate-free conditions, was determined. For this, the $pH_i$ was determined using the pH-sensitive fluorescent dye BCECF (Calbiochem, where the precursor BCECF-AM is employed). The cells were first loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the $pH_i$ by means of calibration curves. Differing from the described protocol, the cells were incubated in $NH_4Cl$ buffer (pH 7.4) even in the case of the BCECF loading ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 is established using 1 M NaOH). The intracellular acidification was induced by addition of 975 μl of an NH₄Cl-free buffer to 25 μl aliquots of the cells incubated in NH₄Cl buffer. The rate of pH recovery that followed acidification was recorded for 2 minutes in the case of NHE1, for 5 minutes in the case of NHE2, and for 3 minutes in the case of NHE3. For the calculation of the inhibitory potency of the tested substances, cells were first investigated in buffers in which a complete pH recovery occurred and in buffers in which no pH recovery at all took place. For the complete pH recovery (100%), the cells were incubated in Na⁺-containing buffer (133.8 mM NaCl, 4.7 mM KCl, 1.25 mM CaCl₂, 1.25 mM MgCl₂, 0.97 mM Na₂HPO₄, 0.23 mM NaH₂PO₄, 5 mM hepes, 5 mM glucose, a pH of 7.0 is established using 1 M NaOH). For the determination of the 0% value, the cells were incubated in an Na⁺-free buffer (133.8 mM choline chloride, 4.7 mM KCl, 1.25 mM CaCl₂, 1.25 mM MgCl₂, 0.97 mM K₂HPO₄, 0.23 mM KH₂PO₄ 5 mM hepes, 5 mM glucose, a pH of 7.0 is established using 1 M NaOH). The substances to be tested were prepared in the Na⁺-containing buffer. The recovery of the intracellular pH at any tested concentration of a substance was expressed as a percent of the maximum recovery. From the percentage values of the pH recovery, the $IC_{50}$ value of the respective substance was calculated by means of a Sigma Plot program for the individual NHE subtypes.

TABLE 3

NHE activity

| Example | Rat NHE3 $IC_{50}$ [μM] |
|---|---|
| 1 | 0.34 |
| 5 | 2.9 |
| 6 | 2.1 |

We claim:
1. A substituted heterocyclo-norbornylamino compound having an exo-configuration nitrogen and endo-fused five-membered or six-membered ring of the formula I or having an exo-configuration nitrogen and exo-fused five-membered or six-membered ring of the formula I a,

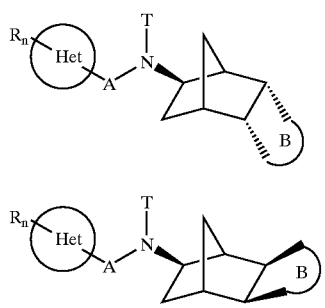

wherein:
 A is $(C_1-C_4)$-alkylene;
 T is $(C_1-C_4)$-alkyl or H;
 B is a saturated or unsaturated carbon five-membered or six-membered ring, which is unsubstituted or is substituted by 1–3 substituents chosen from oxo, hydroxyl, $(C_1-C_4)$-alkoxy, and $(C_1-C_4)$-alkyl;
 Het is a 5- or 6-membered, saturated or unsaturated, heterocycle that contains up to four identical or different heteroatoms chosen from O, S, N, and Se;
 R is OH, F, Cl, Br, I, CN, NO₂, phenyl, CO₂R1, $(C_1-C_4)$-alkyl, $(C_1-C_4)$-alkoxy, amino, $(C_1-C_4)$-alkylamino, di$(C_1-C_4)$-alkylamino, or amino-$(C_1-C_4)$-alkyl, wherein the alkyl radicals are unsubstituted or are completely or partly substituted by fluorine;
 $R_1$ is H or $(C_1-C_4)$-alkyl, which is unsubstituted or completely or partly substituted by fluorine;
 n is 0, 1, 2, 3 or 4,
 wherein, if n=2, 3 or 4, the substituents R are chosen independently of one another;
 or a pharmaceutically tolerable salt or trifluoracetate thereof.

2. A compound as claimed in claim 1, wherein:
 A is $(C_1-C_2)$-alkylene;
 T is H or methyl;
 B is a saturated or unsaturated carbon five-membered or six-membered ring;
 Het is a 5- or 6-membered, saturated or unsaturated, heterocycle that contains up to three identical or different heteroatoms chosen from O, S, and N;
 R is F, Cl, Br, iodine, amino, hydroxymethyl, OH, phenyl, CO₂R1, $(C_1-C_4)$-alkyl, or $(C_1-C_4)$-alkoxy,
 wherein the alkyl radicals are unsubstituted or completely or partly substituted by fluorine;
 $R_1$ is H or $(C_1-C_4)$-alkyl, where the alkyl radical is unsubstituted or completely or partly substituted by fluorine;
 n is 0, 1, 2 or 3,
 where, if n=2 or 3, the corresponding substituents R are chosen independently of one another.

3. A compound as claimed in claim 1, wherein:
 A is $(C_1-C_2)$-alkylene;
 T is hydrogen;
 B is a saturated or unsaturated carbon five-membered or six-membered ring;
 Het is a 5- or 6-membered, saturated or unsaturated, heterocycle that contains up to two identical or different heteroatoms chosen from O, S, and N;
 R is F, Cl, Br, $(C_1-C_4)$-alkoxy, or $(C_1-C_4)$-alkyl, where the alkyl radicals are unsubstituted or completely or partly substituted by fluorine;
 n is 0, 1 or 2, wherein, if n=2, the corresponding substituents R are chosen independently of one another.

4. A compound as claimed in claim 1, chosen from:
 exo/exo-(octahydro-4,7-methanoinden-5-yl)pyridin-3-ylmethylamine,
 (rac)-exo/endo-(octahydro-4,7-methanoinden-5-yl)pyridin-3-ylmethylamine,
 (+)-exo/endo-(octahydro-4,7-methanoinden-5-yl)pyridin-3-ylmethylamine,
 (−)-exo/endo-(octahydro-4,7-methanoinden-5-yl)pyridin-3-ylmethylamine,
 (rac)-exo/endo-(octahydro-4,7-methanoinden-5-yl)pyrazin-2-ylmethylamine,
 (+)-exo/endo-(octahydro-4,7-methanoinden-5-yl)pyrazin-2-ylmethylamine,
 (−)-exo/endo-(octahydro-4,7-methanoinden-5-yl)pyrazin-2-ylmethylamine,
 exo/endo-(decahydro-1,4-methanonaphthalen-2-yl)pyrazin-2-ylmethylamine,
 exo/endo-(octahydro-4,7-methanoinden-5-yl)thiophen-2-ylmethylamine,
 exo/endo-(octahydro-4,7-methanoinden-5-yl)thiophen-3-ylmethylamine,
 exo/endo-(3a,4,5,6,7,7a-hexahydro-3H-4,7-methanoinden-5-yl)pyridin-3-ylmethylamine, exo/endo-(3a,4,5,6,7,7a-hexahydro-1H-4,7-methanoinden-5-yl)pyridin-3-ylmethylamine, exo/endo-furan-3-ylmethyl-(octahydro-4,7-methanoinden-5-yl)amine, exo/endo-furan-2-ylmethyl-(octahydro-4,7-methanoinden-5-yl)amine, exo/endo-(decahydro-1,4-methanonaphthalen-2-yl)pyridin-3-ylmethylamine, exo/endo-(octahydro-4,7-methanoinden-5-yl)-(1H-pyrrol-2-ylmethyl)amine, exo/endo-(octahydro-4,7-methanoinden-5-yl)-pyrimidin-5-ylmethylamine, and their pharmaceutically tolerable salts or trifluoracetates.

5. A compound as claimed in claim 1, chosen from:

exo/exo-(octahydro-4,7-methanoinden-5-yl)pyridin-3-ylmethylamine, (rac)-exo/endo-(octahydro-4,7-methanoinden-5-yl)pyridin-3-ylmethylamine, (+)-exo/endo-(octahydro-4,7-methanoinden-5-yl)pyridin-3-ylmethylamine, (−)-exo/endo-(octahydro-4,7-methanoinden-5-yl)pyridin-3-ylmethylamine, (rac)-exo/endo-(octahydro-4,7-methanoinden-5-yl)pyrazin-2-ylmethylamine, (+)-exo/endo-(octahydro-4,7-methanoinden-5-yl)pyrazin-2-ylmethylamine, exo/endo-(octahydro-4,7-methanoinden-5-yl)thiophen-2-ylmethylamine, exo/endo-(3a,4,5,6,7,7a-hexahydro-3H-4,7-methanoinden-5-yl)pyridin-3-ylmethylamine, exo/endo-(3a,4,5,6,7,7a-hexahydro-1H-4,7-methanoinden-5-yl)pyridin-3-ylmethylamine, exo/endo-(decahydro-1,4-methanonaphthalen-2-yl)pyridin-3-ylmethylamine, exo/endo-(octahydro-4,7-methanoinden-5-yl)-(1H-pyrrol-2-ylmethyl)amine, exo/endo-(octahydro-4,7-methanoinden-5-yl)-pyrimidin-5-ylmethylamine, and their pharmaceutically tolerable salts or trifluoracetates.

6. A process for the preparation of a compound as claimed in claim 1, comprising reacting a compound of the formula (II) or (II a)

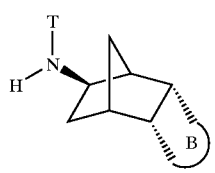

II

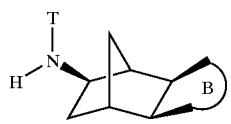

II a with a compound of the formula (III)

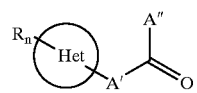

III in the presence of at least one reductant or at least one Lewis acid to give at least one compound of the formula (I) or (I a), wherein, independently of one another, A' corresponds to a bond or $(C_1-C_3)$-alkyl, A" corresponds to H or $(C_1-C_3)$-alkyl, and A' and A" together with the carbon atom of the carbonyl group represent as many carbon atoms as A represents in formula (I) or (I a); and optionally converting the compound of formula (I) or (I a) into a pharmaceutically tolerable salt or trifluoracetate.

7. A process for the preparation of a compound as claimed in claim 1, comprising isolating an intermediate of the formula (IV) or (IV a),

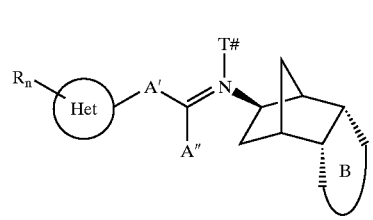

IV

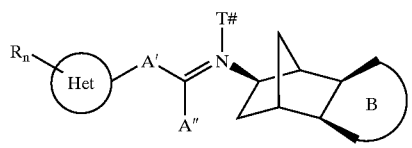

IV a formed from reacting a compound of the formula (II) or (II a)

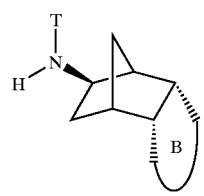

II

II a with a compound of the formula (III),

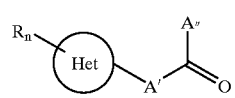

III and then converting the intermediate of the formula (IV) or (IV a) into a compound of the formula (I) or (I a) by using at least one reductant, wherein, independently of one another, A' corresponds to a bond or $(C_1-C_3)$-alkyl, A" corresponds to H or $(C_1-C_3)$-alkyl, and A' and A" together with the carbon atom of the carbonyl group represent as many carbon atoms as A represents in formula (I) or (I a); and wherein T# is a free electron pair or $(C_1-C_4)$-alkyl, and wherein a counterion is assigned to the iminium ion formed when T# is $(C_1-C_4)$-alkyl; and optionally converting the compound of formula (I) or (I a) into a pharmaceutically tolerable salt or trifluoracetate.

8. A process as claimed in claim 7, wherein the counterion assigned to the ammonium nitrogen formed when T# is $(C_1-C_4)$-alkyl is chosen from chloride and tosylate.

9. A process for the preparation of a compound as claimed in claim 1, comprising reacting a compound of the formula (II) or (II a)

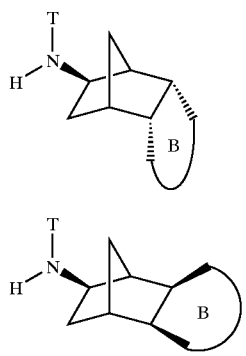

II

II a with an alkylating agent of the formula (V) to produce a compound of the formula (I) or (I a),

V wherein U is a nucleophilically substitutable group and wherein, independently of one another, A' corresponds to a bond or $(C_1-C_3)$-alkyl, A" corresponds to H or $(C_1-C_3)$-alkyl, and A' and A" together with the carbon atom which U is bonded represent as many carbon atoms as A represents in formula (I) or (I a); and optionally converting the compound of formula (I) or (I a) into a pharmaceutically tolerable salt or trifluoracetate.

10. A process as claimed in claim 9, wherein U is chosen from halogen atoms, alkylsulfonates, and arylsulfonates.

11. A process as claimed in claim 10, wherein U is chosen from Cl, Br, I, mesylate, and tosylate.

12. A process for the preparation of a compound as claimed in claim 1, comprising reducing carboxamides of the formula (VI) or (VI a) to the corresponding amines of the formula (I) or (I a),

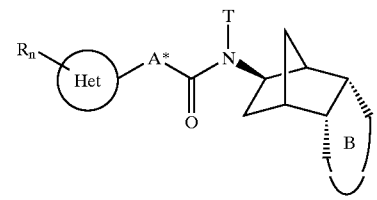

VI

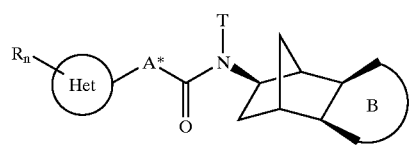

VI a wherein A* corresponds to a bond or $(C_1-C_3)$-alkyl, and optionally converting the compound of formula (I) or (I a) into a pharmaceutically tolerable salt or trifluoracetate.

13. A process for the preparation of a compound as claimed in claim 1, comprising alkylating a compound of the formula (I) or (I a), in which T corresponds to hydrogen, using alkylating agents of the formula (VII), $$T^*—U \qquad \text{VII}$$

wherein T* is $(C_1-C_4)$-alkyl and U is a nucleophilically substitutable group, such that tertiary amines result from this reaction; and optionally converting the compound of formula (I) or (I a) into a pharmaceutically tolerable salt or trifluoracetate.

14. A process as claimed in claim 13, wherein U is chosen from halogen atoms, alkylsulfonates, and arylsulfonates.

15. A process as claimed in claim 14, wherein U is chosen from Cl, Br, I, mesylate, and tosylate.

16. A process for the preparation of a compound as claimed in claim 1, comprising reacting a dicyclopentadienylplatinum complex of the formula (VIII)

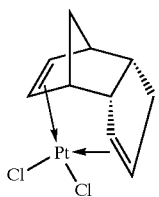

VIII with amines of the formula (IX),

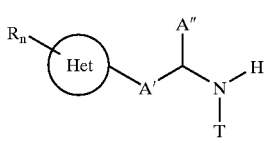

IX and subsequently reducing the intermediate formed to a compound of the formula (I) or (I a)

wherein, independently of one another, A' corresponds to a bond or $(C_1-C_3)$-alkyl, A" corresponds to H or $(C_1-C_3)$-alkyl, and A' and A", together with the carbon atom to which the nitrogen atom is bonded, represent as many carbon atoms as A represents in formula (I), and optionally converting the compound of formula (I) into a pharmaceutically tolerable salt or trifluoroacetate.

17. A composition, comprising at least one compound as claimed in claim 1 and a carrier.

18. A pharmaceutical composition, comprising at least one compound as claimed in claim 1 and a pharmaceutically acceptable carrier.

19. A method for the treatment of a disorder of the respiratory drive, comprising administering to a patient in need thereof a compound as claimed in claim 1.

20. A method according to claim 19, wherein the disorder of the respiratory drive is a sleep-related respiratory disorder.

21. A method according to claim 20, wherein the sleep-related respiratory disorder is sleep apnea.

22. A method for the treatment of snoring, comprising administering to a patient in need thereof a compound as claimed in claim 1.

23. A method for the treatment of acute or chronic kidney disorders, comprising administering to a patient in need thereof a compound as claimed in claim 1.

24. A method according to claim 23, wherein the acute or chronic kidney disorder is chosen from acute kidney failure and chronic kidney failure.

25. A method for the treatment of disorders of the intestinal function, comprising administering to a patient in need thereof a compound as claimed in claim 1.

26. A method for the treatment of disorders of the bile function, comprising administering to a patient in need thereof a compound as claimed in claim 1.

27. A method for the treatment of an ischemic condition of the peripheral or central nervous system, or an ischemic condition due to a stroke, comprising administering to a patient in need thereof a compound as claimed in claim 1.

28. A method for the treatment of an ischemic condition of a peripheral organ or a limb, comprising administering to a patient in need thereof a compound as claimed in claim 1.

29. A method for the treatment of an ischemia-induced endogenous state of shock, comprising administering to a patient in need thereof a compound as claimed in claim 1.

30. A method for the protection of an organ during a surgical operation or an organ transplantation, comprising administering to a patient in need thereof a compound as claimed in claim 1.

31. A method for the conservation or storage of an organ to be transplanted, comprising storing said organ in a solution comprising a compound as claimed in claim 1.

32. A method for the treatment of a disease in which cell proliferation is a primary or secondary cause, comprising administering to a patient in need thereof a compound as claimed in claim 1.

33. A method for the treatment of a disorder of lipid metabolism, comprising administering to a patient in need thereof a compound as claimed in claim 1.

34. A method for the treatment of an infestation by an ectoparasite, comprising administering to a patient in need thereof a compound as claimed in claim 1.

* * * * *

UNITED STATES PATENT AND TRADEMARK OFFICE
CERTIFICATE OF CORRECTION

PATENT NO.    : 6,737,423 B2
DATED         : May 18, 2004
INVENTOR(S)   : Uwe Heinelt et al.

It is certified that error appears in the above-identified patent and that said Letters Patent is hereby corrected as shown below:

Title page,
Item [57], ABSTRACT,
Line 11, "is chemically" should read -- ischemically --.

Column 31,
Line 9, after "(I a);" delete "and".

Signed and Sealed this

Twenty-first Day of December, 2004

JON W. DUDAS
*Director of the United States Patent and Trademark Office*